(12) United States Patent
Terrell et al.

(10) Patent No.: US 12,084,701 B2
(45) Date of Patent: Sep. 10, 2024

(54) BIOFABRICATION OF ADVANCED FUNCTIONAL MATERIALS USING BACTERIAL CELLULOSE SCAFFOLDS

(71) Applicant: U.S. Army Combat Capabilities Development Command, Army Research Labortary, Adelphi, MD (US)

(72) Inventors: Jessica L. Terrell, Philadelphia, PA (US); Justin P. Jahnke, Bethesda, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 550 days.

(21) Appl. No.: 17/148,720

(22) Filed: Jan. 14, 2021

(65) Prior Publication Data
US 2022/0220521 A1    Jul. 14, 2022

(51) Int. Cl.
| | | |
|---|---|---|
| *C12P 19/04* | (2006.01) | |
| *B01J 35/33* | (2024.01) | |
| *C01B 32/05* | (2017.01) | |
| *C08L 1/02* | (2006.01) | |

(52) U.S. Cl.
CPC ............... *C12P 19/04* (2013.01); *B01J 35/33* (2024.01); *C01B 32/05* (2017.08); *C08L 1/02* (2013.01)

(58) Field of Classification Search
None
See application file for complete search history.

(56) References Cited

U.S. PATENT DOCUMENTS

| | | |
|---|---|---|
| 8,785,623 B2 | 7/2014 | Olsson et al. |
| 10,073,087 B2 | 9/2018 | Deng et al. |
| 2022/0220521 A1* | 7/2022 | Terrell ............... C08L 1/02 |

FOREIGN PATENT DOCUMENTS

| | | |
|---|---|---|
| CN | 102634068 B | 4/2014 |
| CN | 103922301 B | 11/2015 |

* cited by examiner

*Primary Examiner* — Christian L Fronda
(74) *Attorney, Agent, or Firm* — Emily C. Moscati

(57) ABSTRACT

A biofabrication method for producing cellulose-based materials. The method includes providing active cellulose-producing bacteria such as *Gluconacetobacter* and culturing media in a container; combining organic additives or inorganic additives with the active cellulose-producing bacteria in the container to produce a cellulose hydrogel matrix composed of entangled bacteria-produced cellulose nanofibers; controlling a concentration of the additives in the cellulose hydrogel matrix; and exposing the cellulose hydrogel matrix in selected thermal environment to create a biofabricated functional material.

13 Claims, 19 Drawing Sheets

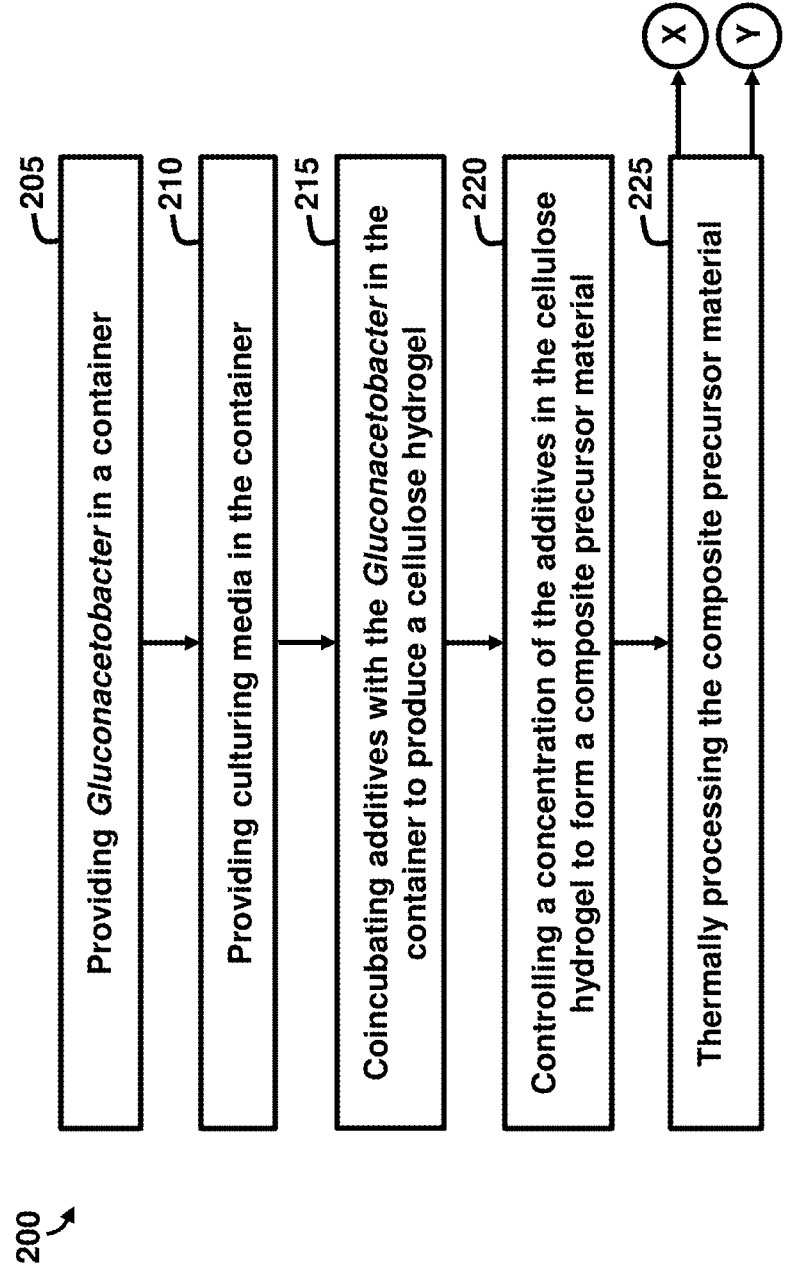

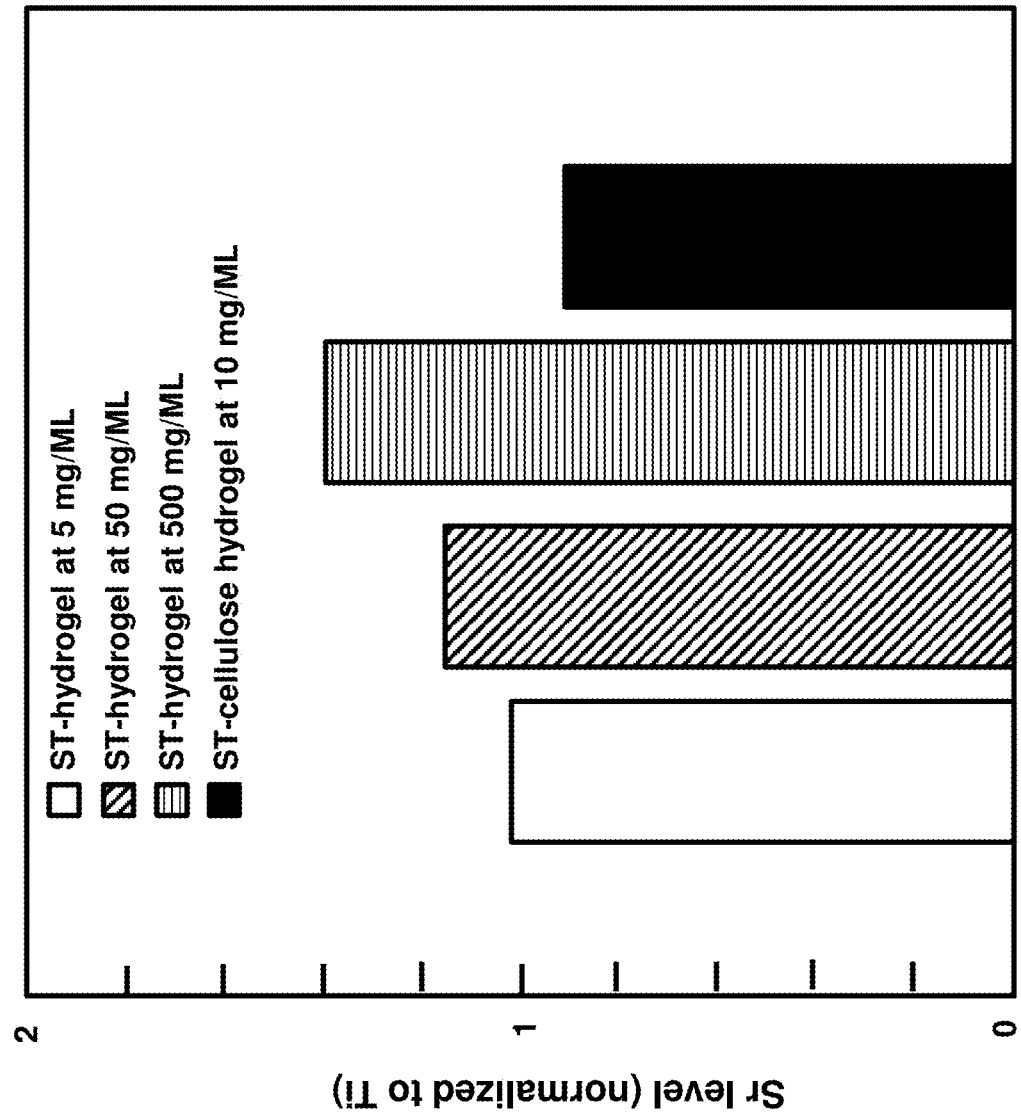

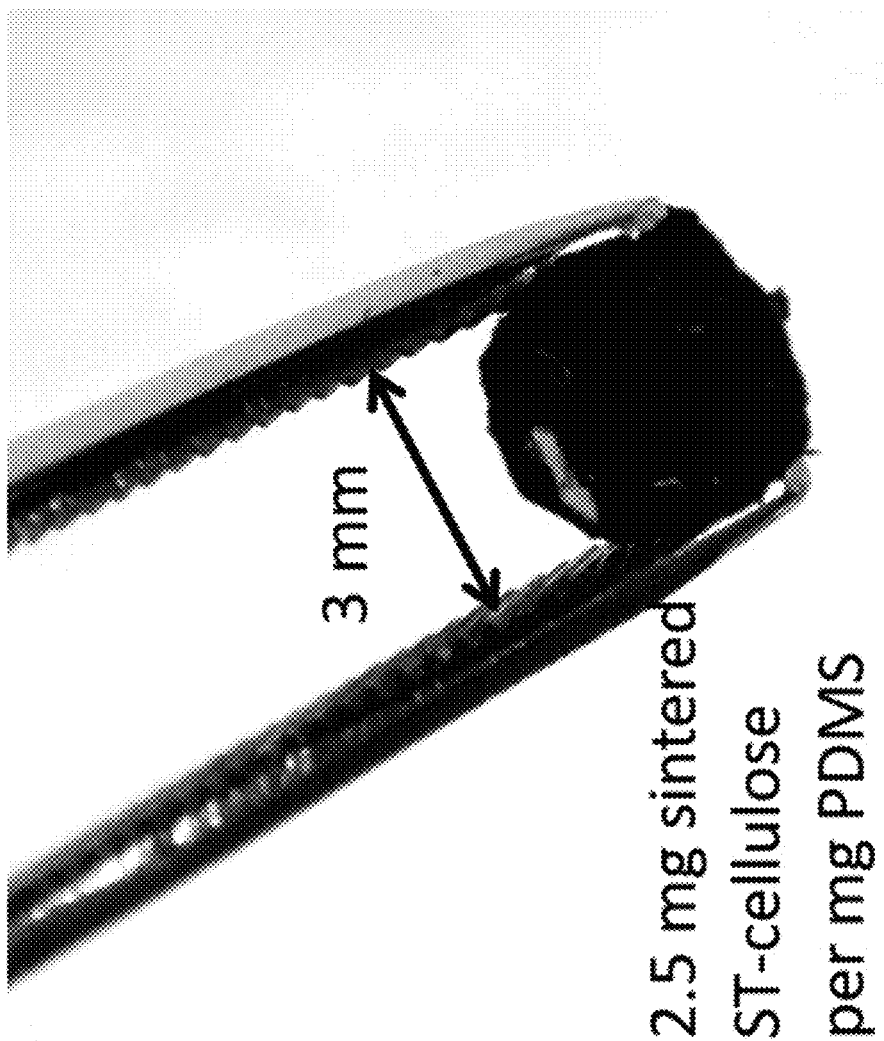

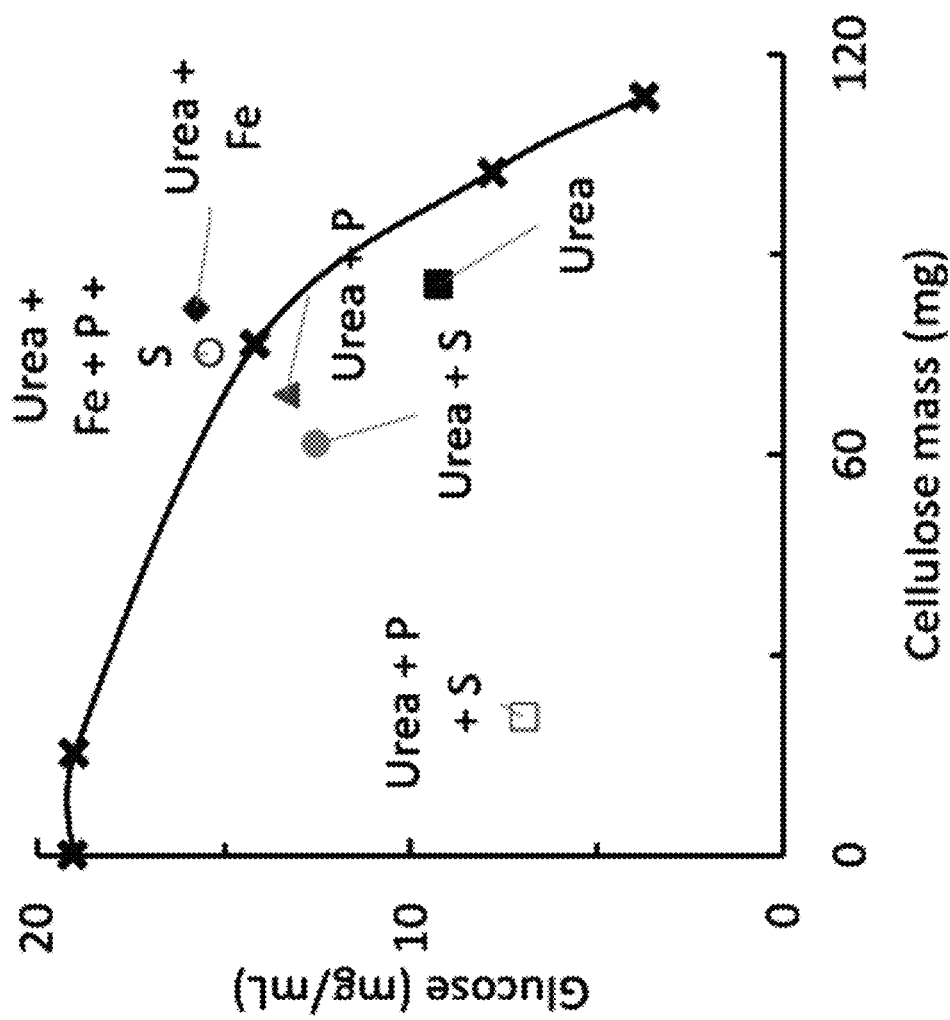

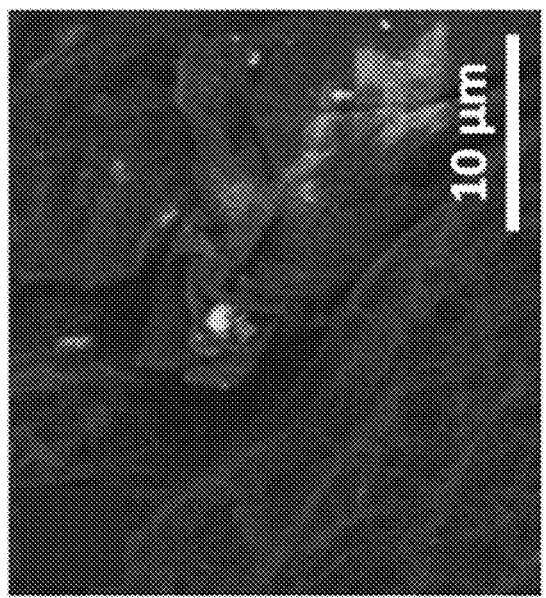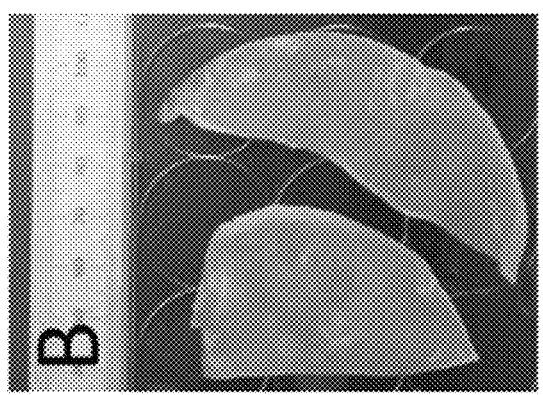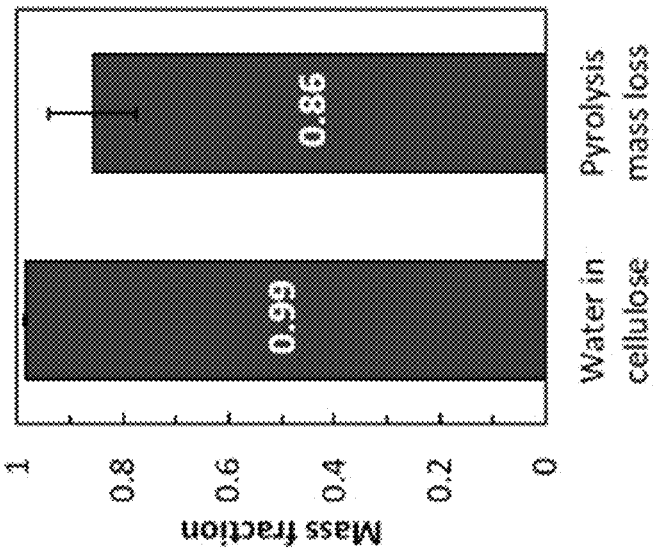

BIOFABRICATION OF ADVANCED FUNCTIONAL MATERIALS USING BACTERIAL CELLULOSE SCAFFOLDS

GOVERNMENT INTEREST

The embodiments herein may be manufactured, used, and/or licensed by or for the United States Government without the payment of royalties thereon.

BACKGROUND

Technical Field

The embodiments herein generally relate to biofabrication techniques, and more particularly to biofabrication techniques to create composite materials.

Description of the Related Art

Plant-derived cellulose materials have been used as metal organic frameworks for energy storage applications, and, when carbonized, metal-free catalysts and filtration systems. Traditional fabrication approaches typically require significant processing steps to render the material useful for a device. To achieve nanoparticle-incorporated bacterial cellulose, prior strategies have included addition of nanoparticles to media during static culture or post-growth particle synthesis through alkaline precipitation (e.g., for iron oxides) or chemical oxidation of bacterial cellulose for reactivity with silver salts to form silver nanoparticle coatings. Conventionally, carbon networks (i.e., graphene-like materials) are obtained from bacterial cellulose after it is cultivated and purified. To dope the carbon with other elements, conventional methodologies use absorption of polysaccharide-staining dyes (e.g., methylene blue, Congo red, both of which are sulfur and nitrogen-containing compounds) prior to pyrolyzing the material.

It is generally challenging to fabricate 3-dimensional porous scaffolds for high-surface area materials. Conventional techniques generally require chemical processing of plant biomass to obtain cellulose nanofibers followed by their chemical crosslinking. Moreover, functionalization of cellulose materials typically requires many steps and the use of harsh chemicals. Limited conventional methods exist for tethering functional groups to polymer/cellulose scaffolds. Furthermore, these techniques are generally difficult to control with nano/micro precision. Additionally, conventional chemical processing techniques typically use harsh chemicals and conditions as well as strict environments (e.g., cleanroom). Moreover, it is generally difficult to uniformly impregnate porous materials with nanoparticles or functionalization reagents in a top-down way. Accordingly, there is a need for a new biofabrication technique to produce composite materials that overcomes the limitations of the conventional solutions.

SUMMARY

In view of the foregoing, an embodiment herein provides a method of producing cellulose-based structures, the method comprising providing bacteria in a container; providing media in the container to sustain the bacteria; combining additives with the bacteria to produce a cellulose nanofiber; controlling a concentration of the additives in the cellulose nanofiber to create a uniform distribution of the additives in the cellulose nanofiber; and processing the cellulose nanofiber at a selected temperature to create a composite material. The bacteria may comprise *Gluconacetobacter*. The additives may comprise organic additives.

The organic additives may comprise any of compounds, click handle analogs, carbon/oxide particles, biopolymers, and catalytic enzymes. The biopolymers may comprise any of proteins, carbohydrates, and nucleic acids. The additives may comprise inorganic additives. The inorganic additives may comprise any of metal nanoparticles, metal oxides, and metal salts. The cellulose nanofiber may be modified during production through any of diffusion, binding, and surface modification of fibers constituting the cellulose nanofiber. The controlling of the concentration of the additives may occur by purifying the cellulose nanofiber by solvent exchange to diffuse away extra additives. The controlling of the concentration of the additives may occur by evaporating the cellulose nanofiber to enhance the concentration of the additives within the cellulose nanofiber. The processing of the cellulose nanofiber at the selected temperature may comprise freeze-drying the cellulose nanofiber. The freeze-drying of the cellulose nanofiber may create a dehydrated material. The processing of the cellulose nanofiber at the selected temperature may comprise performing pyrolysis on the cellulose nanofiber. The performing of the pyrolysis on the cellulose nanofiber may create a carbonized material.

Another embodiment provides a biofabrication method comprising providing *Gluconacetobacter* in a container; providing culturing media in the container; coincubating additives with the *Gluconacetobacter* in the container to produce a cellulose hydrogel; controlling a concentration of the additives in the cellulose hydrogel to form a composite precursor material; and thermally processing the composite precursor material. The additives may comprise a chemical compound or salt as a source of nitrogen, iron, phosphorous, sulfur, or other chemical element of interest for impregnation or nanoparticle formation. The method may comprise forming a metallized aerogel from the thermally processed composite precursor material. The method may comprise forming a doped electrocatalyst from the thermally processed composite precursor material. The coincubating of the additives with the *Gluconacetobacter* in the container may occur at a temperature range between approximately 20-30° C.

Another embodiment provides a biofabrication method for producing cellulose-based materials, the method comprising providing active cellulose-producing bacteria and culturing media in a container; combining organic additives or inorganic additives with the active cellulose-producing bacteria in the container to produce a cellulose hydrogel matrix composed of entangled bacteria-produced cellulose nanofibers; controlling a concentration of the additives in the cellulose hydrogel matrix; and exposing the cellulose hydrogel matrix in selected thermal environment to create a biofabricated functional material.

These and other aspects of the embodiments herein will be better appreciated and understood when considered in conjunction with the following description and the accompanying drawings. It should be understood, however, that the following descriptions, while indicating exemplary embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 3A is a flow diagram illustrating a biofabrication method, according to an embodiment herein;

FIG. 6C is a graph illustrating stoichiometric ratios of the atomic percentage of strontium (Sr) to titanium (Ti), according to an embodiment herein;

FIG. 6D is an image of a bulk dielectric material, according to an embodiment herein;

FIG. 7C is a graph illustrating cellulose mass vs. residual glucose, according to an embodiment herein;

FIG. 8A is a graph illustrating measurements of cellulose mass, according to an embodiment herein;

FIG. 8B are images of cellulose hydrogel materials, according to an embodiment herein;

FIG. 8C is a scanning electron micrograph of a cellulose hydrogel material, according to an embodiment herein;

DETAILED DESCRIPTION

Figure 1:
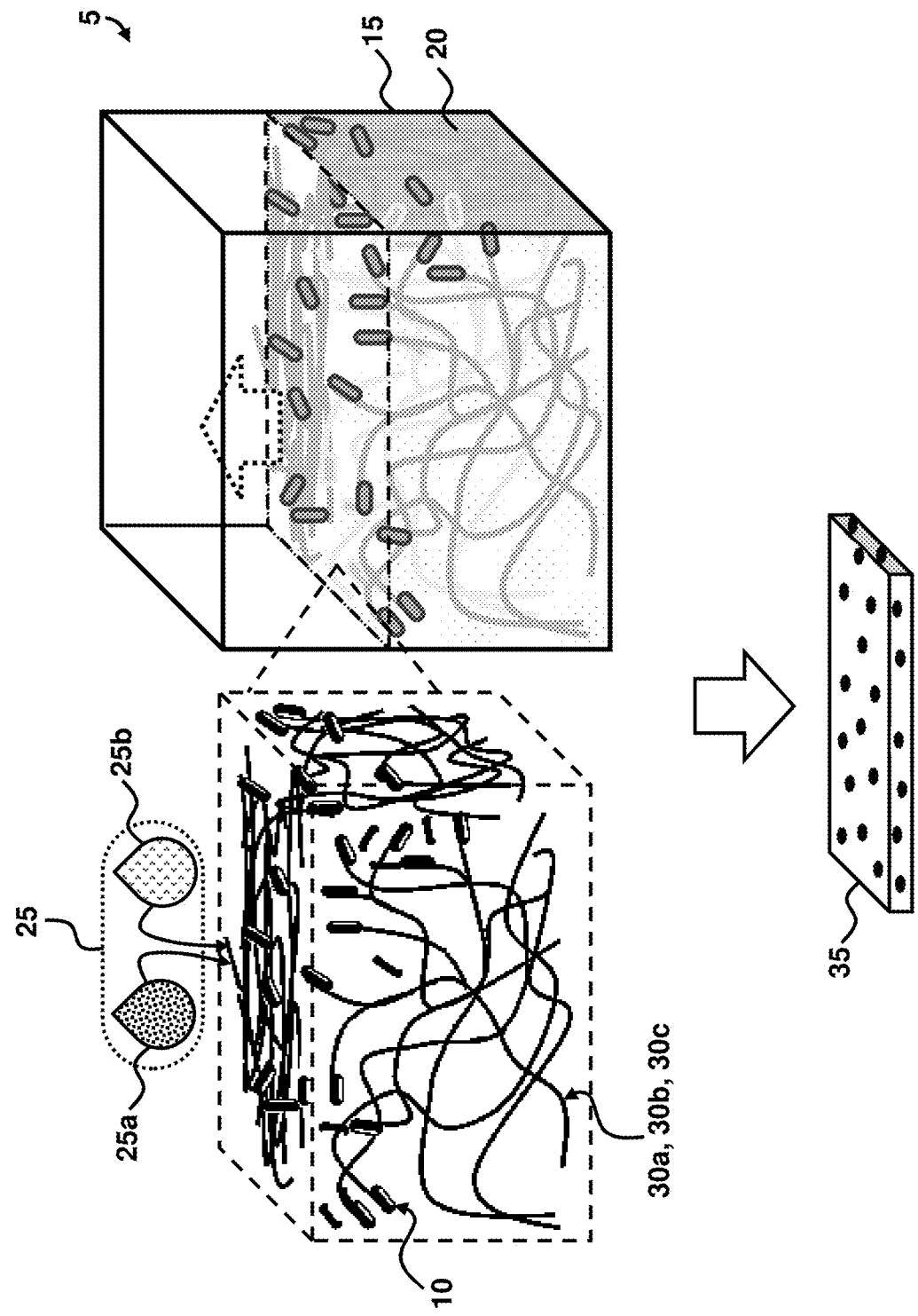
FIG. 1 is a schematic diagram illustrating an apparatus for producing cellulose-based structures, according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

It will be understood that when an element or layer is referred to as being "on", "connected to", or "coupled to" another element or layer, it may be directly on, directly connected to, or directly coupled to the other element or layer, or intervening elements or layers may be present. In contrast, when an element or layer is referred to as being "directly on", "directly connected to", or "directly coupled to" another element or layer, there are no intervening elements or layers present. It will be understood that for the purposes of this disclosure, "at least one of X, Y, and Z" may be construed as X only, Y only, Z only, or any combination of two or more items X, Y, and Z (e.g., XYZ, XYY, XZ, ZY, YZ, XX, YY, ZZ, etc.).

The embodiments herein provide a biofabrication workflow to assemble precursors of functional materials using an in situ-produced bacterial cellulose scaffold and added components. Biocompatible fabrication methodologies include the innate cellulose production characteristics of bacterial species *Gluconacetobacter* and principles of biologically-mediated precision binding and hierarchical assembly. Since the biofabrication steps occur autonomously and in an ambient environment (cellulose accumulation, binding interactions for self-assembly, passive diffusion and incorporation in aqueous solution and room temperature), the techniques provided by the embodiments herein simplify the fabrication process for several materials (e.g., with dielectrics and electrocatalysts, for example). Conventional workflows may require user-based fabrication of a polymeric aerogel framework, surface chemistry and chemical grafting protocols, and organic/aqueous solvent exchanges with challenges in scalability, shaping, and composite uniformity. Additionally, in conventional techniques, the cellulose is typically recovered and purified before functionalization, which presents additional fabrication steps, the use of harsh chemicals, similar challenges in composite uniformity and limitations to nanofiber functionalization. Referring now to the drawings, and more particularly to FIGS. 1 through 10, where similar reference characters denote corresponding features consistently throughout the figures, there are shown preferred embodiments. In the drawings, the size and relative sizes of components, layers, and regions, etc. may be exaggerated for clarity.

Figure 2:
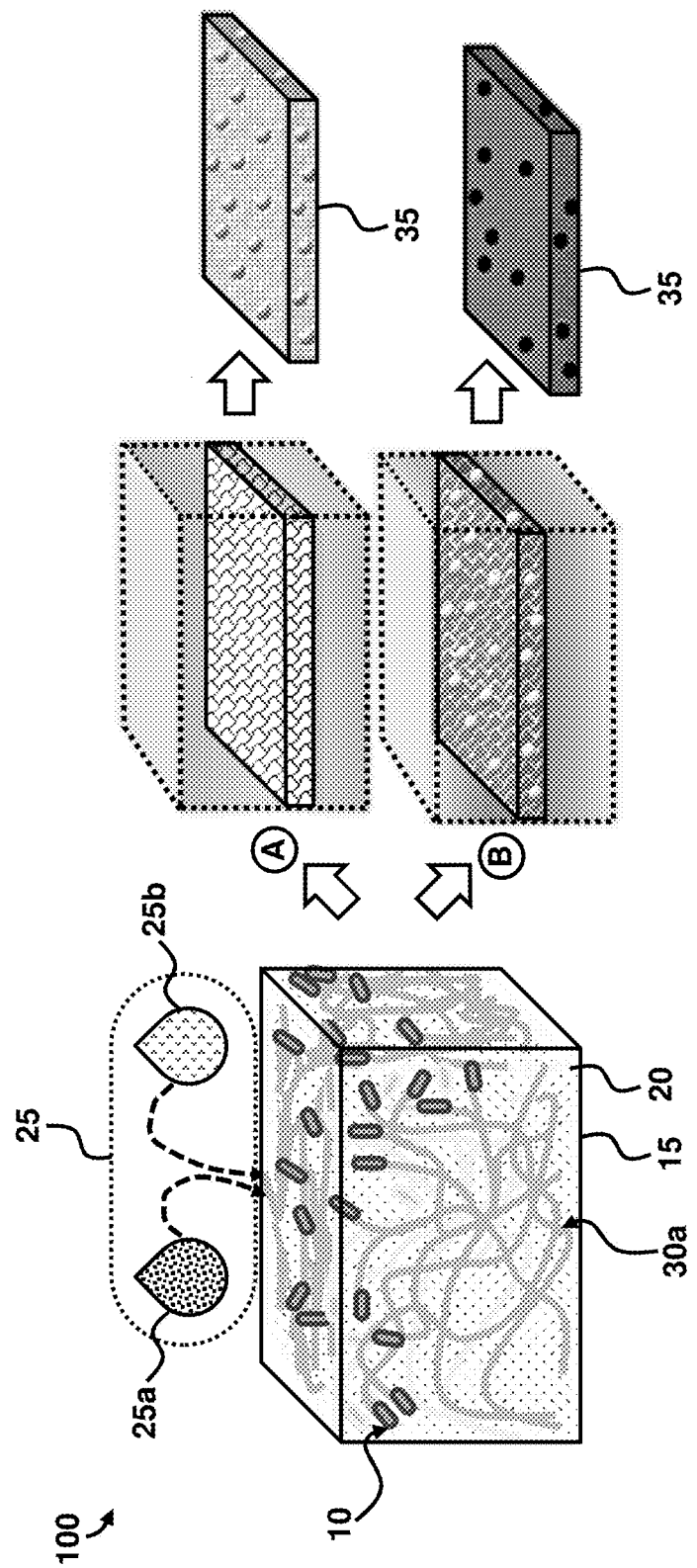
FIG. 2 is a schematic diagram illustrating a workflow for producing cellulose-based structures, according to an embodiment herein.

FIG. 1 illustrates an apparatus 5 for producing cellulose-based structures according to the workflow of FIG. 2. Bacteria 10 is provided in a container 15. In an example, the container may comprise a culture chamber, such as one made from plastic or glass. According to an example, the bacteria 10 may comprise *Gluconacetobacter*. Other types of bacteria may also be used in accordance with the embodiments herein. Culturing media 20 is provided in the container 15 to sustain the bacteria 10. In some examples, the culturing media 20 may aid in the growth of the bacteria 10 in the container 15. Additives 25 are combined with the bacteria 10 to produce a cellulose nanofiber product, referred to herein as cellulose nanofiber 30a. According to an example, the cellulose nanofiber 30a may be modified during production through any of diffusion, binding, and surface modification of fibers constituting the cellulose nanofiber 30a. The bacteria 10 fabricates a scalable matrix of nano-cellulose (e.g., cellulose nanofiber 30a), which is a desirable framework material that presents advantages over its commonly used alternative-plant-derived cellulose. In an example, the additives 25 may comprise organic additives 25a. In this regard, the organic additives 25a may comprise any of compounds, click handle analogs, carbon/oxide particles, biopolymers, and catalytic enzymes. In an example, the biopolymers may comprise any of proteins, carbohydrates, and nucleic acids. According to another example, the additives 25 may comprise inorganic additives 25b. In this regard, the inorganic additives 25b may comprise any of metal nanoparticles, metal oxides, and metal salts. For example, nanoparticles can be uniformly incorporated into the cellulose nanofiber 30a in a bio-friendly way, without chemical treatments. Instead, the additives 25 (e.g., such as nanoparticles, etc.) are coincubated with the bacteria 10 to distribute them during cellulose generation. Furthermore, the additives 25 (e.g., such as nanoparticles, etc.) can be readily tethered/functionalized to the nanofibers using the cellulose-binding fusion proteins. The dotted arrow shown in FIG. 2 represents the direction of cellulose pellicle growth at the air/water interface.

The biopolymers such as fusion proteins could be assembled onto the bacterial cellulose nanofiber 30a and tailored to tether nanoparticles onto the cellulose nanofiber 30a. In an example, strontium titanate could be incorporated into cellulose nanofiber 30a in a biocompatible manner, recovered for sintering, and tested to yield dielectric performance with desirable high permittivity properties. Alternatively, supplementing bacterial nutrient broth with elements of interest (in the form of salts), which, once carbonized, become doped with the elements and provide desirable performance as an electrocatalyst for oxygen reduction reactions. The supplements do not deter growth or cellulose accumulation.

The workflow further includes controlling a concentration of the additives 25 in the cellulose nanofiber 30a to create a uniform distribution of the additives 25 in the cellulose nanofiber 30a. In an example, the controlling of the concentration of the additives 25 may occur (A) by purifying the cellulose nanofiber 30a by solvent exchange to diffuse away extra additives 25. In another example, the controlling of the concentration of the additives 25 may occur (B) by evaporating the cellulose nanofiber 30a to enhance the concentration of the additives 25 within the cellulose nanofiber 30a.

Thereafter, the cellulose nanofiber 30a is processed at a selected temperature to create a composite material 35. The processing of the cellulose nanofiber 30a at the selected temperature may comprise freeze-drying the cellulose nanofiber 30a. In an example, the freeze-drying of the cellulose nanofiber 30a may create a dehydrated material (e.g., the composite material 35 may be configured as a dehydrated material). In another example, the processing of the cellulose nanofiber 30a at the selected temperature may comprise performing pyrolysis on the cellulose nanofiber 30a. The performing of the pyrolysis on the cellulose nanofiber 30a may create a carbonized material (e.g., the composite material 35 may be configured as a carbonized material). The production of the advanced functional composite material 35 from the cellulose nanofiber 30a may occur under conditions compatible with the culturing of the Gluconacetobacter bacteria 10.

The workflow creates readily-formed cellulose composite precursors in conjunction with Gluconacetobacter propagation and cellulose production in the culturing media 20 by utilizing biofabrication principles and straightforward material recovery steps prior to post-processing. Bacterial cellulose scaffolds are functionalized in situ using additives 25 of biocompatible composition and concentration supplemented in the growth media 20 upon inoculation. Additives 25 (especially biological components) may facilitate binding interactions and hierarchical assembly of components directly onto the cellulose scaffold (e.g., cellulose nanofiber 30a). In this way, the additives 25 readily incorporate with the cellulose nanofiber 30a as it is generated.

The cellulose composite material 35 having additives 25 incorporated therein may be recovered using solvent exchange or solvent concentration. As indicated in FIG. 2, solvent exchange (A) can be used when scaffold functionalization is desired in order to eliminate unbound, superfluous additives 25, and retaining a composite material 35 with immobilized functional components. Conversely, as indicated in FIG. 2, solvent concentration (B) allows additives 25 to be enriched within the cellulose scaffold at concentrations that do not support bacterial growth but are preferred once cellulose has accumulated to a sufficient biomass. Subsequent post-processing steps are minimal steps (e.g., freeze-drying for a dehydrated material or pyrolysis for a carbonized material) to achieve materials suitable for advanced applications.

Figure 3B:
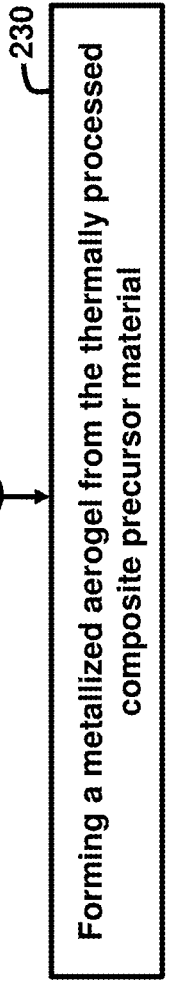
FIG. 3B is a flow diagram illustrating a method of forming a metallized aerogel, according to an embodiment herein.
Figure 3C:
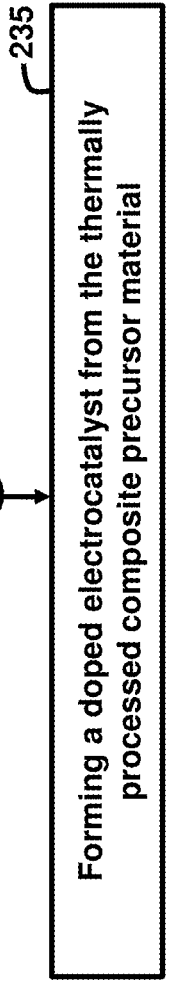
FIG. 3C is a flow diagram illustrating a method of forming a doped electrocatalyst, according to an embodiment herein.

FIGS. 3A through 3C, with reference to FIGS. 1 and 2, are flow diagrams illustrating a biofabrication method 200. As shown in FIG. 3A, the biofabrication method 200 comprises providing (205) bacteria 10 such as Gluconacetobacter in a container 15; providing (210) culturing media 20 in the container 15; and coincubating (215) additives 25 with the Gluconacetobacter in the container 15 to produce a moldable cellulose hydrogel 30b. In an example, the cellulose hydrogel 30b comprises entangled bacteria-produced cellulose nanofibers 30a. The coincubation of the additives 25 with the Gluconacetobacter may occur through diffusion, binding, or surface modification of the cellulose nanofibers 30a. Next, the biofabrication method 200 comprises controlling (220) a concentration of the additives 25 in the cellulose hydrogel 30b to form a composite precursor material 35; and thermally processing (225) the composite precursor material 35. The composite cellulose hydrogel 30b can be purified by solvent exchange to diffuse away superfluous additives 25 or conversely evaporated to enhance the concentration of the additives 25 within the cellulose hydrogel 30b.

In an example, the additives 25 may comprise a chemical compound or salt as a source of nitrogen, iron, phosphorous, sulfur, or other chemical element of interest for impregnation or nanoparticle formation. According to an example, the coincubating (215) of the additives 25 with the Gluconacetobacter in the container 15 may occur at a temperature range between approximately 20-30° C. As shown in FIG. 3B, the method 200 may comprise forming (230) a metallized aerogel from the thermally processed composite precursor material 35. As shown in FIG. 3C, the method 200 may comprise forming (235) a doped electrocatalyst from the thermally processed composite precursor material 35. The in situ biofabrication method 200 of the cellulose composite precursors promotes uniform distribution of functional components, takes advantage of the cellulose nanofiber network for autonomous generation of a high surface area 3D composite precursor material 35, and as a result, enables a simplified fabrication workflow.

The establishment of binding specificity between constituents facilitates hierarchical self-assembly (e.g., affinity interactions, nucleic acid hybridization, biorthogonal click chemistry, etc.), with simple elimination of superfluous unassembled constituents from the cellulose hydrogel by solvent exchange. Alternatively, by evaporating the culture media 20, the additive 25 reaches a desired concentration that is uniformly distributed within the cellulose hydrogel 30b. Thus, both solvent-exchanged and solvent-concentrated cellulose hydrogels presents a composite precursor material 35 that can be obtained via the two-step process (e.g., biofabrication and recovery). The bacterial cellulose hydrogel 30b can be readily customized into molded shapes by the corresponding shape and configuration of the culturing container 15 and uniformly biofunctionalized with fusion proteins, uniquely providing nanoscale visual resolution of the "living" material and nanofiber functionality.

Since the steps of the biofabrication method 200 occur autonomously and in an ambient environment (e.g., cellulose accumulation, binding interactions for self-assembly, passive diffusion and incorporation in aqueous solution and room temperature), the method 200 simplifies the fabrication process for several materials (e.g., with dielectrics and electrocatalysts, etc.). Conventional biofabrication workflows may require user-based fabrication of a polymeric aerogel framework, surface chemistry and chemical grafting protocols, and organic/aqueous solvent exchanges with challenges in scalability, shaping, and composite uniformity. Additionally, in conventional techniques that use bacterial cellulose scaffolds, the cellulose is typically recovered and purified before functionalization, which presents additional fabrication steps, the use of harsh chemicals, similar challenges in composite uniformity, and limitations to nanofiber functionalization, all of which such limitations are overcome using the biofabrication method 200 provided by the embodiments herein.

Figure 4:
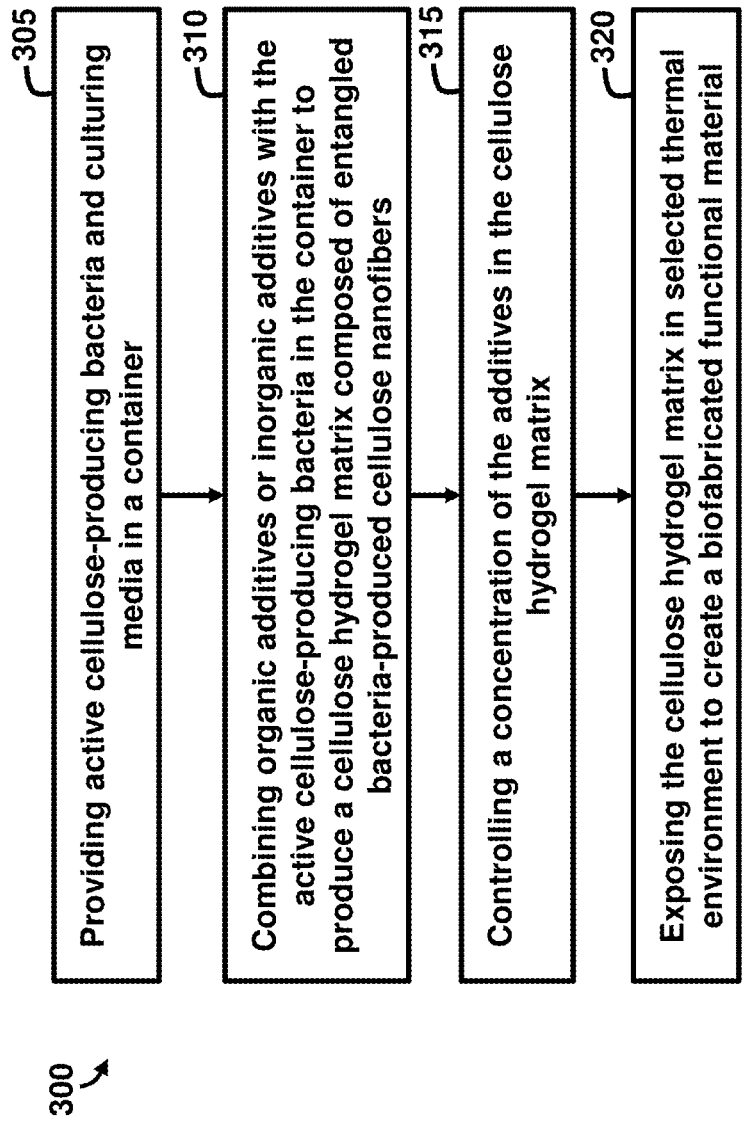
FIG. 4 is a flow diagram illustrating a biofabrication method for producing cellulose-based materials, according to an embodiment herein.

FIG. 4, with reference to FIGS. 1 through 3C, is a flow diagram of a biofabrication method 300 for producing cellulose-based materials. The method 300 comprises providing (305) active cellulose-producing bacteria 10 and culturing media 20 in a container 15; combining (310) organic additives 25a or inorganic additives 25b with the active cellulose-producing bacteria 10 in the container 15 to produce a cellulose hydrogel matrix 30c composed of entangled bacteria-produced cellulose nanofibers 30a; controlling (315) a concentration of the additives 25 in the cellulose hydrogel matrix 30c; and exposing (320) the cellulose hydrogel matrix 30c in selected thermal environment to create a biofabricated functional material (e.g., composite material 35). To customize the cellulose functionality for various applications, functional moieties (e.g., organic additives 25a or inorganic additives 25b such as nanoparticles, etc.) are either bound directly to the matrix fibers (e.g., using fusion proteins) or passively incorporated as the bacteria 10 produce the cellulose hydrogel matrix 30c. Upon recovery of the cellulose hydrogel matrix 30c, the solution components (e.g., the additives 25 and entangled bacteria-produced cellulose nanofibers 30a) can be further concentrated into the cellulose hydrogel matrix 30c by evaporating the solution. Thus, preparation of the precursor composite material 35 includes a set-up of the bacteria 10 in the culturing media 20 containing desired components for the composite material 35, and specialized recovery of the composite material 35 upon its in situ formation. The final composite material 35 utilizes only minimal post-processing steps for typical downstream applications such as metallized aerogels, doped electrocatalysts, etc. (e.g., freeze-drying for dehydration or pyrolysis to carbonize the composite material 35).

The biofabrication method 300 and recovery steps produce advanced functional materials (e.g., composite material 35) from bacterial cellulose (e.g., cellulose hydrogel matrix 30c composed of entangled bacteria-produced cellulose nanofibers 30a). The biofabrication can be defined as a process of using biomaterial building blocks (e.g., cells and biopolymers like proteins, nucleic acids, and polysaccharides) and benign assembly methodologies (e.g., binding interactions, enzymatic grafting) that occur in ambient solvents and temperatures to retain biological functionality. In this case, cellulose composite precursors can be readily formed in conjunction with *Gluconacetobacter* propagation and cellulose production in preferred growth culturing media 20. This in situ fabrication of cellulose composite precursors promotes uniform distribution of functional components, takes advantage of the cellulose nanofiber network for autonomous generation of a high surface area 3D material, and as a result, enables a simplified fabrication workflow. Protein and peptide binding interactions with both cellulose nanofibers (e.g., fusion proteins containing a cellulose binding module (CBM) such as one derived from *Clostridium thermocellum*) and functional components (e.g., inorganic-binding peptides, peptides that promote mineralization) can be used to functionalize cellulose nanoscaffolds with inorganic particles (e.g., ferromagnetic, dielectric particles). The supplementation of growth culturing media 20 with added elements, combined with post-growth media concentration as the recovery step, establishes a novel strategy to generate superior precursors for doped carbonized aerogels while supporting bacterial culture growth. The unique biofabrication strategies yield material precursors that are challenging to fabricate by other methods, and when post-processed, demonstrate functional properties (e.g., high dielectric permittivity, electrocatalytic oxygen reduction efficiency) that are superior to previously-reported metrics for similar, conventional materials.

Figure 5:
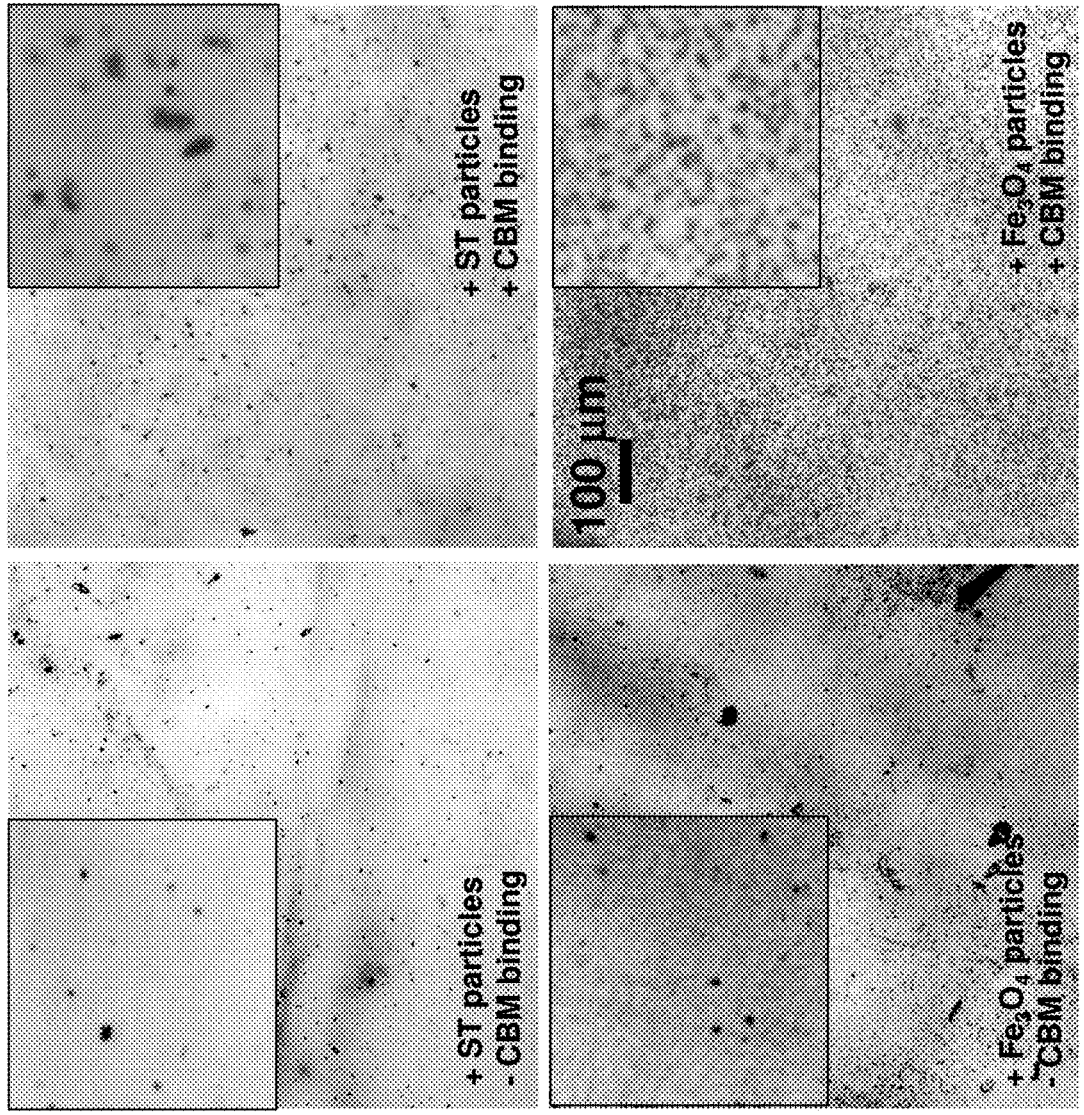
FIG. 5 are microscopic images of cellulose hydrogels bonded to nanoparticles, according to an embodiment herein.

*Gluconacetobacter* shaking cultures may be used with added nanoparticles (such as, for example, strontium titanate (ST) or iron oxide ($Fe_3O_4$)) for direct incorporation into the cellulose hydrogel 30b. FIG. 5, with reference to FIGS. 1 through 4, demonstrates the enhanced binding affinity of ST and $Fe_3O_4$ particles to cellulose hydrogels 30b by including His10-sfGFP-CBM fusion protein with affinity to both the nanoparticles (via His10) and cellulose nanofibers 30a (via CBM), imaged by brightfield microscopy with magnified inset images.

Figure 6A:
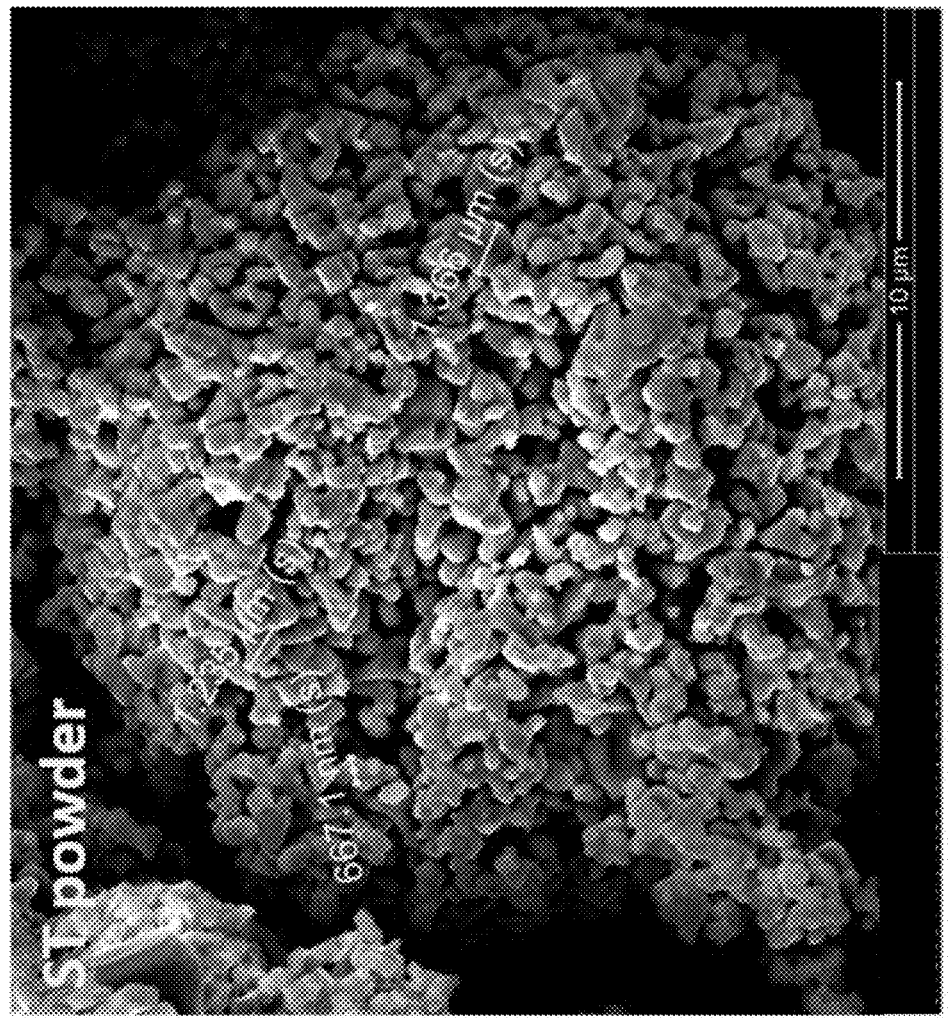
FIG. 6A is a scanning electron micrograph of strontium titanate (ST) powder, according to an embodiment herein.
Figure 6B:
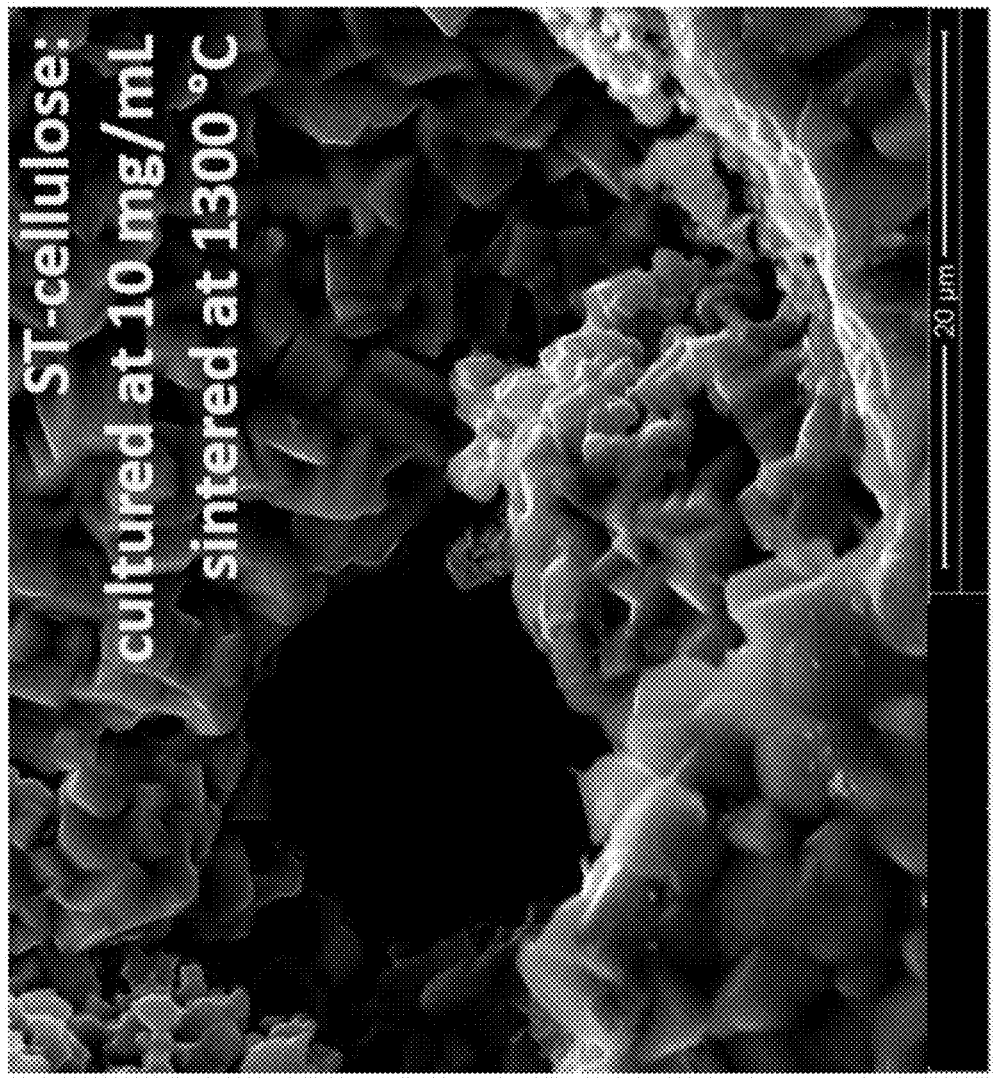
FIG. 6B is a is a scanning electron micrograph of a sintered ST-cellulose composite material, according to an embodiment herein.

The resulting biofabricated cellulose-nanoparticle composite material 35 is scalable to achieve functional materials having desirable properties. In an example, biofabricated cellulose-ST is formed into a capacitor material with a measured dielectric constant that is superior to values of conventional bulk materials. FIGS. 6A and 6B, with reference to FIGS. 1 through 5, depict scanning electron micrographs of (FIG. 6A) ST powder and (FIG. 6B) a sintered ST-cellulose composite sample (prepared at 1300° C. under inert atmosphere for 1+h). FIG. 6C, with reference to FIGS. 1 through 6B, illustrates stoichiometric ratios of the atomic percentage of strontium (Sr) to titanium (Ti) (analyzed by energy dispersive x-ray spectroscopy) for sintered samples prepared either ST entrapped in an inert hydrogel (using 5, 50, or 500 mg/ML ST) or ST entrapped in cellulose via bacterial culturing (using 10 mg/ML ST). FIG. 6D, with reference to FIGS. 1 through 6C, illustrates an example of a bulk dielectric material made by filling ST-cellulose with polydimethylsiloxane (PDMS) using the techniques provided by the embodiments herein.

Figure 7A:
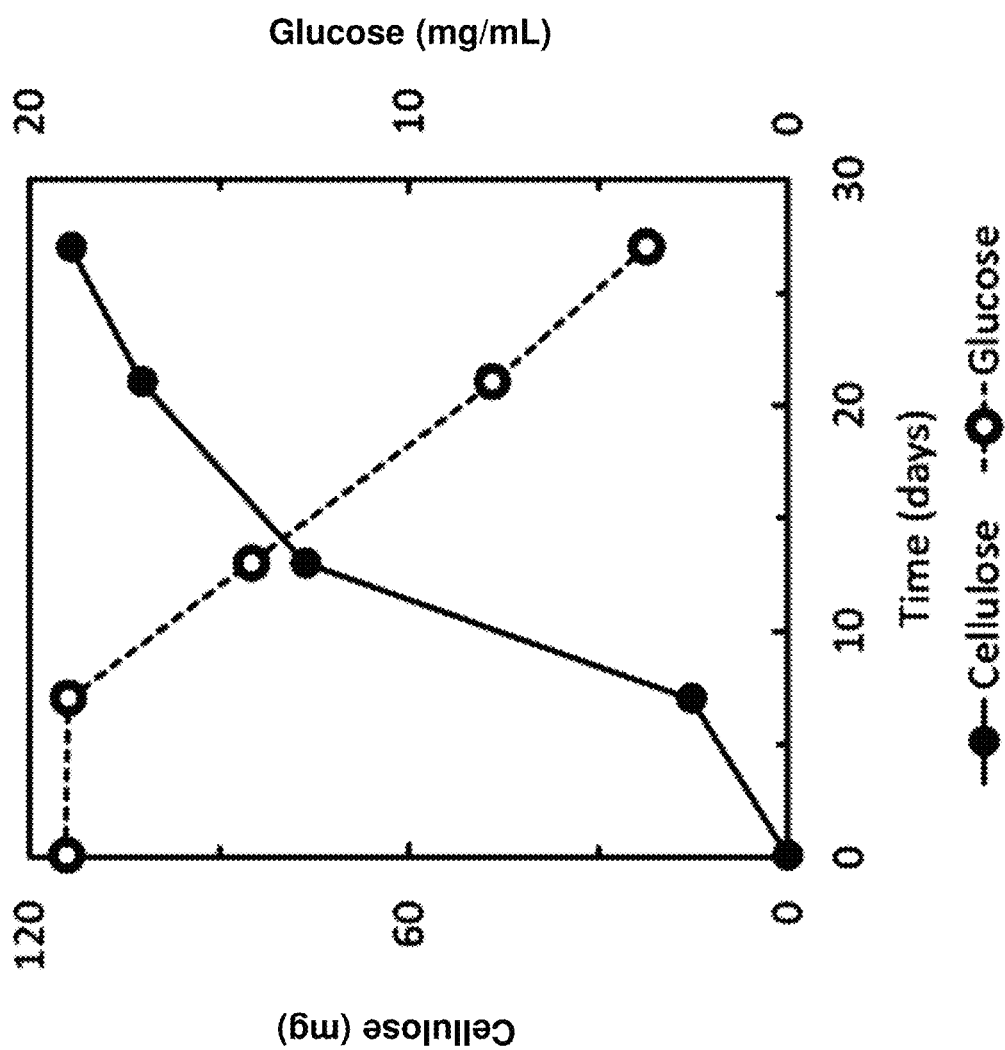
FIG. 7A is a graph illustrating timecourse monitoring of *Gluconacetobacter* productivity, according to an embodiment herein.
Figure 7B:
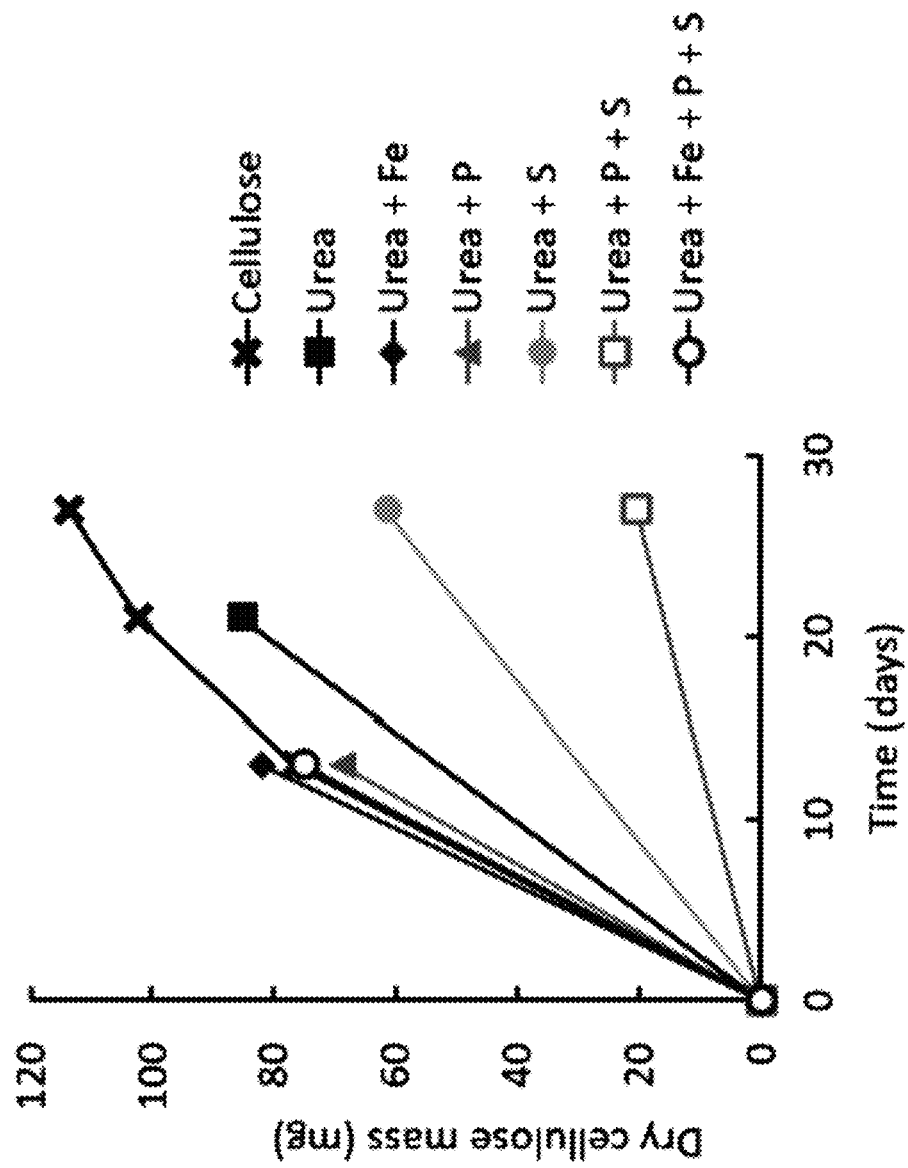
FIG. 7B is a graph illustrating measurements of a cellulose biomass, according to an embodiment herein.

The workflow 100 and biofabrication methods 200, 300 simplify the doping conditions by coincubation of additives 25 (e.g. such as urea and iron chloride for N and Fe doping) with the bacteria 10 such as *Gluconacetobacter*, without the need for material purification and impregnation with chemicals. This provides a bio-friendly approach, and maintains efficient cellulose production as indicated by the experimental results shown in FIGS. 7A through 7C, with reference to FIGS. 1 through 6D. FIG. 7A depicts timecourse monitoring of *Gluconacetobacter* productivity through measurements of glucose depletion rate and cellulose biomass accumulation rate. FIG. 7B illustrates measurements of a cellulose biomass produced by cultures containing various elemental additives 25 (e.g., urea, iron chloride (Fe), sodium phosphate (P), and sodium sulfate (S)). FIG. 7C illustrates a plot of cellulose mass vs. residual glucose in a nutrient media 20 for cultures with elemental additives 25.

Figure 8E:
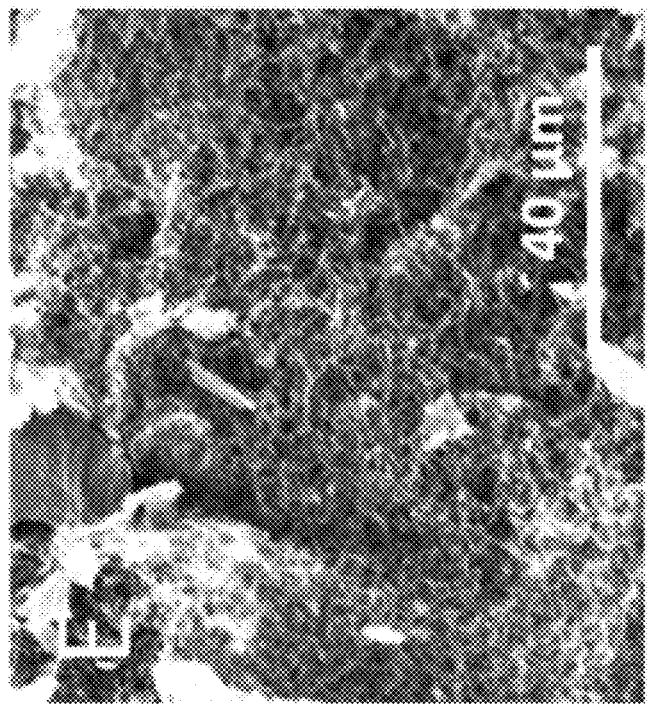
FIG. 8E is a scanning electron micrograph of a carbonized material, according to an embodiment herein.
Figure 8D:
FIG. 8D are additional images of carbonized cellulose materials, according to an embodiment herein.

Using the techniques provided by the embodiments herein, both the bulk structure (molded 3D shapes) and porous nanostructure may be retained in carbonized bacterial cellulose as demonstrated in FIGS. 8A through 8E, with reference to FIGS. 1 through 7C. FIG. 8A illustrates measurements of a cellulose mass after freeze-drying to determine the water content of cellulose hydrogel and of a carbonized product after pyrolysis. FIG. 8B is an image of representative cellulose hydrogel shapes and FIG. 8C is a scanning electron micrograph of cellulose after freeze-drying. FIG. 8D is an image of representative cellulose shapes after pyrolysis and FIG. 8E is a scanning electron micrograph of the resulting carbonized nanonetwork.

Figure 9A:
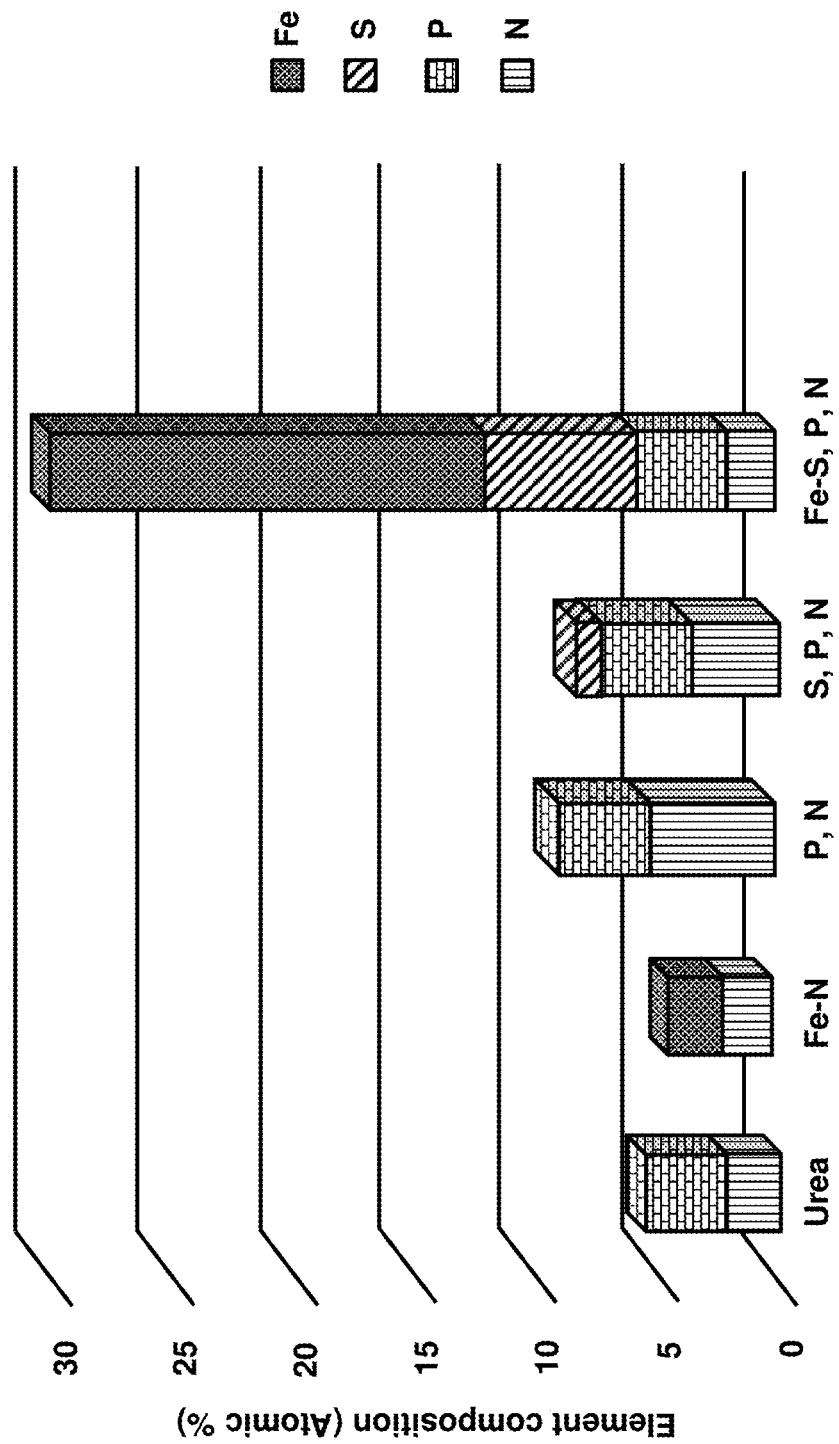
FIG. 9A is a graph illustrating the composition of cellulose derived mesoporous carbons, according to an embodiment herein.
Figure 9B:
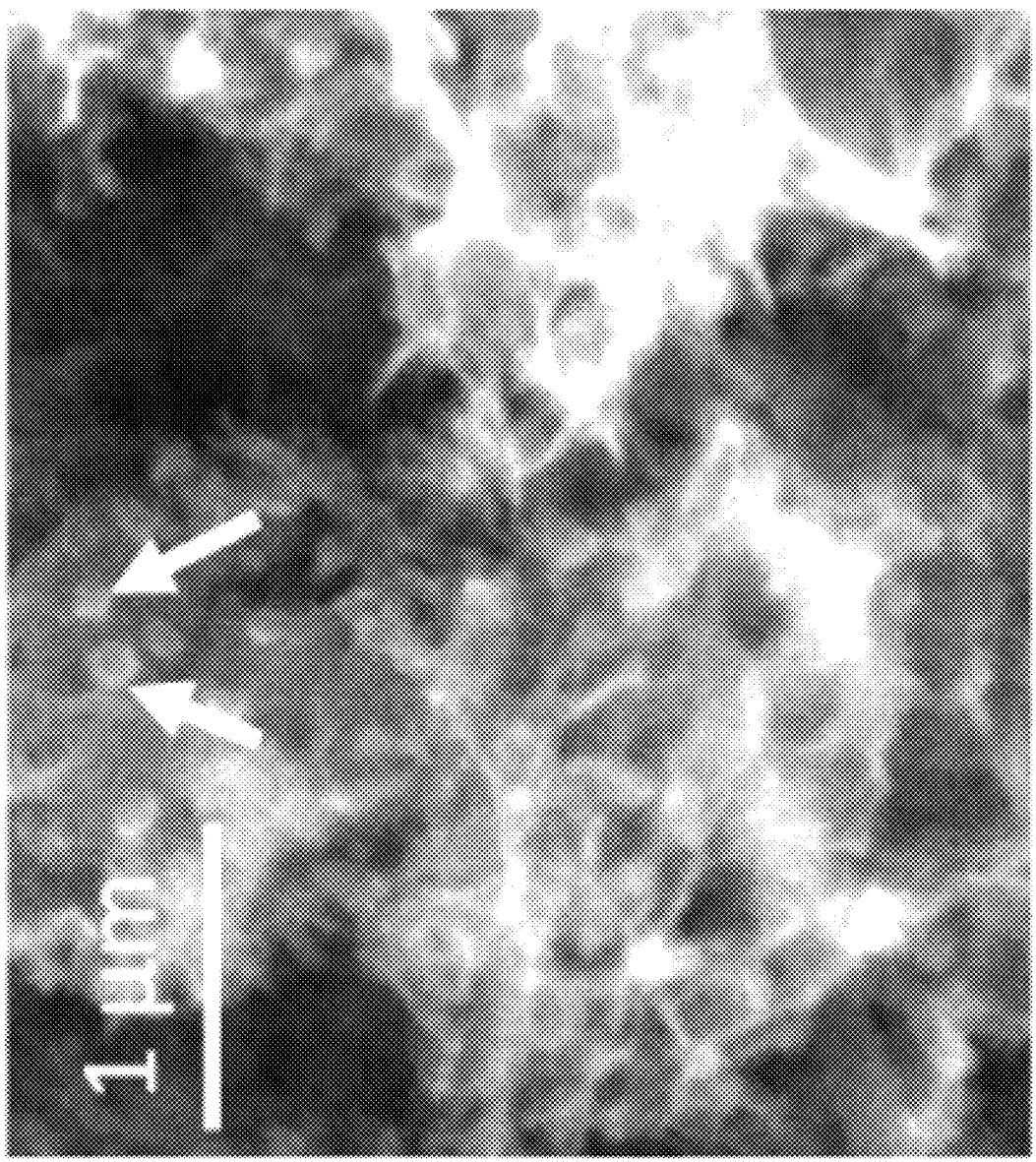
FIG. 9B is a scanning electron micrograph of Fe—S,P,N carbons, according to an embodiment herein.
Figure 9C:
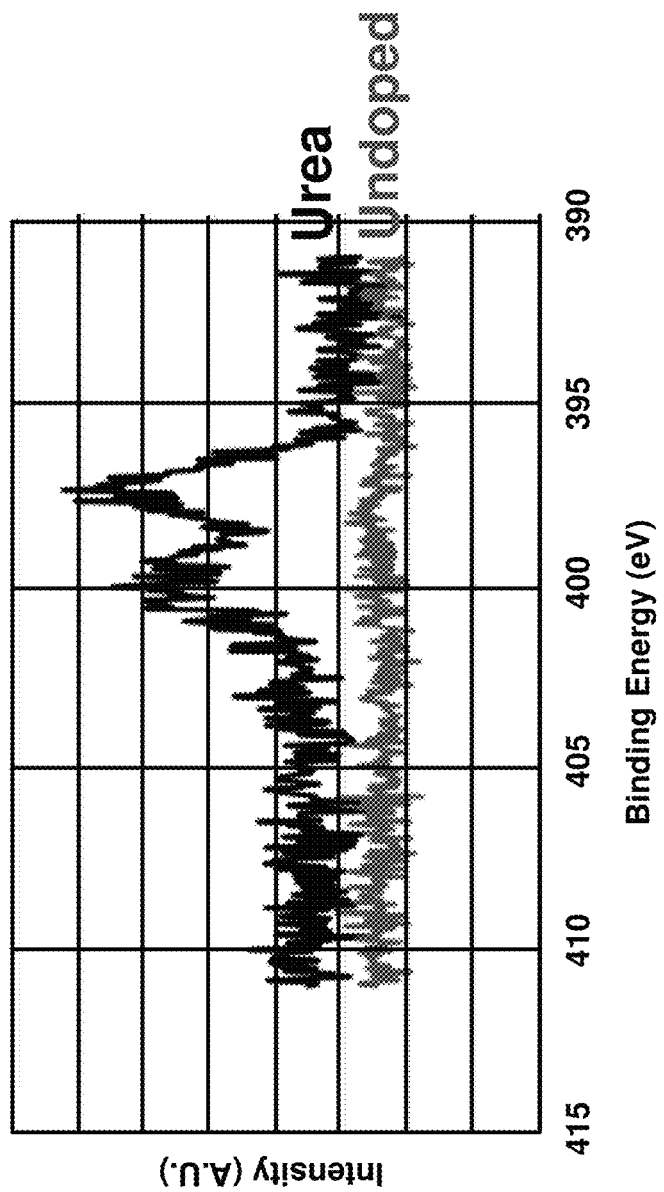
FIG. 9C is a graph illustrating X-ray photoelectron spectroscopy (XPS) data for urea-doped and undoped cellulose derived carbons, according to an embodiment herein.

Through material characterization, experimental results are demonstrated in effectively and uniformly doped carbon networks, as shown in FIGS. 9A through 9C, with reference to FIGS. 1 through 8E. FIG. 9A illustrates elemental composition of cellulose derived mesoporous carbons, as determined by energy-dispersive X-ray spectroscopy (EDS). Catalytic active elements are plotted, with the residual mostly carbon with some oxygen and salt. FIG. 9B is a SEM image of Fe—S, P, N carbons. The arrows draw attention to several nanoparticles formed during processing. FIG. 9C illustrates XPS data for urea-doped and undoped cellulose derived carbons. Almost no residual nitrogen is observed in the undoped sample while the urea doped sample has a peak at 398 eV, indicative of catalytically active pyridinic nitrogen.

Figure 10:
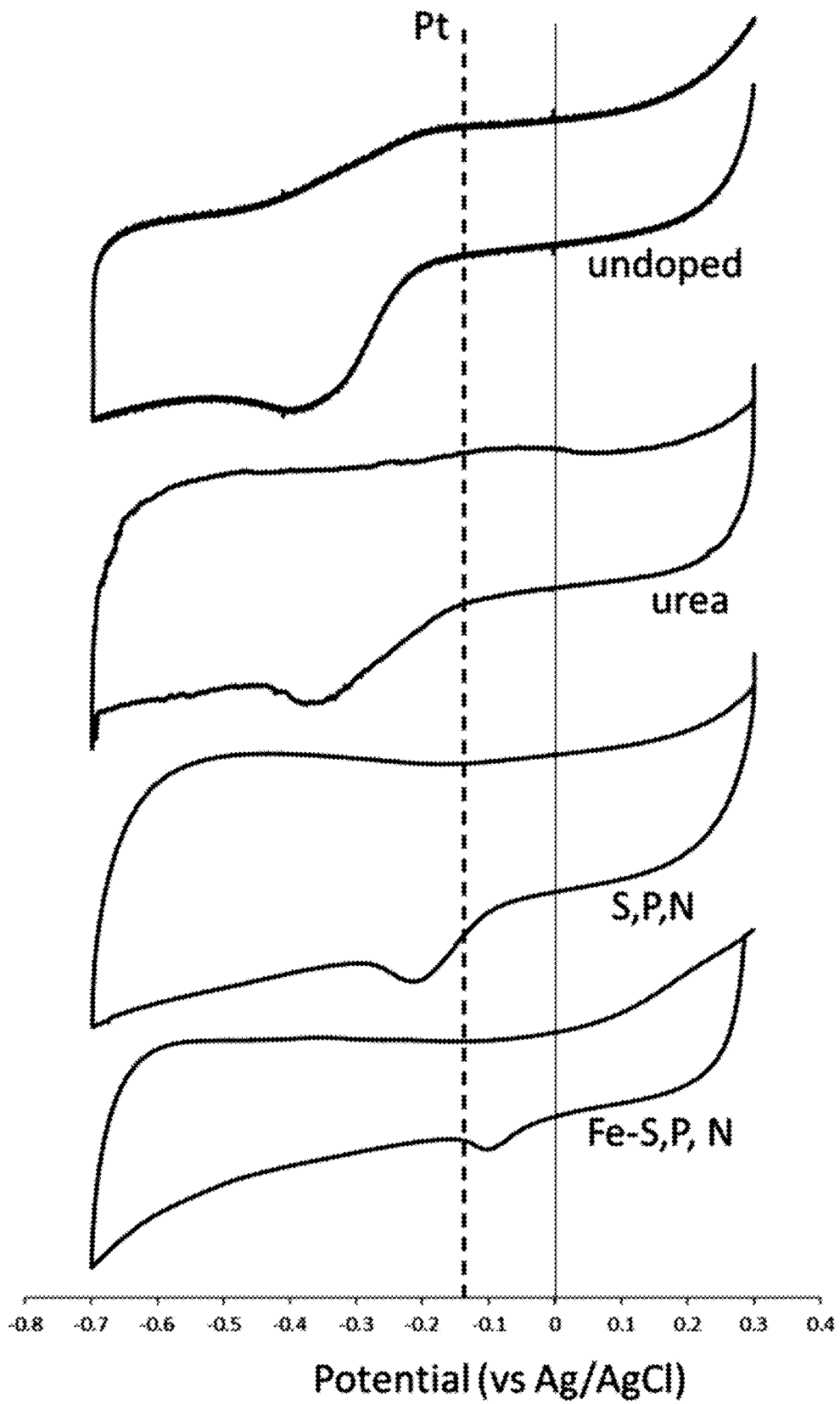
FIG. 10 are cyclic voltammagrams obtained on cellulose-derived carbons where various chemicals are provided during growth to impart particular elements to the resulting material, according to an embodiment herein.

Electrocatalyst materials traditionally require precious metals (e.g., platinum, etc.) for high density energy technologies like fuel cells and batteries. Biofabricated doped carbonized bacterial cellulose provides a much cheaper metal-free alternative electrocatalyst material with electrochemical performance that matches a platinum standard. FIG. 10, with reference to FIGS. 1 through 9C, illustrates cyclic voltammagrams obtained on cellulose-derived carbons that where various chemicals during growth to impart particular elements to the resulting material. The undoped sample is prepared using the *Gluconacetobacter* in a culturing growth media 20, while the other three traces have been doped with: nitrogen (urea), sulfur, phosphorous and nitrogen (S, P, N), or iron along with the other elements (Fe—S, P, N).

The *Gluconacetobacter* bacteria 10 may be used to produce a bulk composite material 35 with the desired porosity and nanofiber aspect ratios. The in situ functionalization through the biofabrication workflow 100 and methods 200, 300, which occur in ambient conditions with minimal user intervention, eliminate the purification and crosslinking/grafting steps inherent in the conventional solutions. By in situ biofabrication, functionalization occurs as the cellulose nanofiber 30a is directly generated by the bacteria 10, resulting in a uniform composite material 35. Moreover, the use of biomolecules for functionalization supply many binding interactions with high specificity that enables fine-tuned control, patterning, and hierarchical assembly.

The techniques provided by the embodiments herein are highly versatile for functionalization of porous nanofiber scaffolds with biological moieties, nanoparticles, and elements. The combination of cellulose with customized functional groups could benefit a variety of applications including renewable energy conversion and high-density storage technology (e.g., fuel cells, batteries, supercapacitors). Furthermore, the embodiments herein may be used for next-generation conformal materials used for interacting with electromagnetic wavelengths (absorption, transmission, etc.) for vehicles, robots, etc. Additionally, the embodiments herein may be used for filters and/or catalysts for protection against and remediation of contaminants or bio/chemical agent neutralization. Moreover, the embodiments herein may be used for biomedical dressings for tissue engineering and wound treatment, according to various examples.

The embodiments herein enable fabrication of new iterations of commercial and military-relevant materials and for point-of-need preparation. Oxygen reduction reaction (ORR) catalyst and high emissivity (c) materials may be produced using the techniques provided by the embodiments herein and provide applications of energy storage/conversion, and materials for electronic warfare devices. Specifically, the ORR catalyst has direct application for anion exchange membrane (AEM) fuel cells and batteries (e.g., Zn-Air) and demonstrates that general utility towards preparing electrocatalysts, which can find applications beyond energy storage, for example, chemical agent amelioration. The embodiments herein provide a "green" workflow that eliminates the use of harsh chemicals, minimizes processing steps, and does not need to use nanoparticles or other additives in excess since they are directly incorporated in situ.

The templating of $SrTiO_3$ nanostructures allows lightweight, high dielectric constant materials for next generation commercial and military equipment and vehicles. Furthermore, the embodiments herein are applicable for many types of nanoparticles, with related compounds (e.g. barium titanate (BT) and barium strontium titanate (BST), etc.) being specifically useful for capacitors for high-power applications. In addition to the applications enabled by the embodiments herein, bacterial cellulose has a range of attractive properties, including low weight, high mechanical toughness and good thermal insulation that make it an attractive platform for commercial and military manufacturing in resource limited environments. For example, the development of high dielectric materials is also of considerable commercial interest, especially when integrated with conventional and 3D printing-based processing.

The embodiments herein provide a technique for the preparation of composite materials 35 by using a bacterial cellulose source (e.g., cellulose nanofiber 30a, cellulose hydrogel 30b, or cellulose hydrogel matrix 30c) that provides an aerogel/high surface area framework, which is a deviation from conventional solutions where cellulose fibers from plants are crosslinked to generate such structures. Moreover, the embodiments herein have utility for "low profile" conformal materials for energy storage/conversion and electromagnetic signal maintenance. The autonomous, in situ biofabrication approach enables such materials to be assembled remotely, such as from a minimal bacterial inoculum "seed" that can be scaled up at the point of need. This approach will also continue to leverage and intersect with the emerging field of genetic engineering/synthetic biology to facilitate complexity in the biofabrication steps performed by a living cellulose-producing culture of bacteria, such as spatiotemporal patterning.

The foregoing description of the specific embodiments will so fully reveal the general nature of the embodiments herein that others may, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein may be practiced with modification within the spirit and scope of the appended claims.

What is claimed is:

1. A method of producing cellulose-based structures, the method comprising:
   providing cellulose-producing bacteria in a container;
   providing media in the container to sustain the cellulose-producing bacteria for cellulose nanofiber production and formation into a cellulose structure;
   combining additives with the cellulose-producing bacteria to introduce the additives to the cellulose structure;
   producing a composite cellulose-based structure through diffusion, binding, and surface modification between the additives and the cellulose nanofiber;
   controlling a concentration of the additives in the composite cellulose-based structure to create a uniform distribution of the additives throughout the composite cellulose-based structure; and
   processing the composite cellulose-based structure at a selected temperature to complete the cellulose-based structure.

2. The method of claim 1, wherein the cellulose-producing bacteria comprises *Gluconacetobacter*.

3. The method of claim 1, wherein the additives comprise organic additives.

4. The method of claim 3, wherein the organic additives comprise any of compounds, click handle analogs, carbon/oxide particles, biopolymers, and catalytic enzymes.

5. The method of claim 4, wherein the biopolymers comprise any of proteins, carbohydrates, and nucleic acids.

6. The method of claim 1, wherein the additives comprise inorganic additives.

7. The method of claim 6, wherein the inorganic additives comprise any of metal nanoparticles, metal oxides, and metal salts.

8. The method of claim 1, wherein the controlling of the concentration of the additives occurs by purifying the cellulose nanofiber by solvent exchange to diffuse away extra additives.

9. The method of claim 1, wherein the controlling of the concentration of the additives occurs by evaporating the cellulose nanofiber to enhance the concentration of the additives within the cellulose nanofiber.

10. The method of claim 1, wherein the processing of the cellulose nanofiber at the selected temperature comprises freeze-drying the cellulose nanofiber.

11. The method of claim 10, wherein the freeze-drying of the cellulose nanofiber creates a dehydrated material.

12. The method of claim 1, wherein the processing of the cellulose nanofiber at the selected temperature comprises performing pyrolysis on the cellulose nanofiber.

13. The method of claim 12, wherein the performing of the pyrolysis on the cellulose nanofiber creates a carbonized material.

* * * * *